United States Patent [19]
von Daehne

[11] Patent Number: 4,511,512
[45] Date of Patent: Apr. 16, 1985

[54] SUBSTANTIALLY PURE DICYCLOHEXYL AMMONIUM 6-β-BROMO-PENICILLANATE

[75] Inventor: Welf von Daehne, Rungsted Kyst, Denmark

[73] Assignee: Leo Pharmaceutical Products Ltd. A/S (Lovens Kemiske Produktionsaktienselskab), Ballerup, Denmark

[21] Appl. No.: 145,880

[22] Filed: May 1, 1980

[51] Int. Cl.³ ............... C07D 499/00; A61K 31/425
[52] U.S. Cl. .......................................... 260/245.2 R
[58] Field of Search ............... 260/245.2 R; 424/270, 424/271

[56] References Cited

U.S. PATENT DOCUMENTS

| | | | |
|---|---|---|---|
| 4,180,506 | 12/1979 | Pratt | 260/245.2 |
| 4,203,993 | 5/1980 | Gordon | 260/245.2 R |
| 4,234,579 | 11/1980 | Barth | 260/245.2 R |
| 4,256,733 | 3/1981 | Barth | 260/245.2 R |
| 4,347,182 | 8/1982 | Gidding et al. | 260/245.2 R |
| 4,397,783 | 8/1983 | Kellogg et al. | 260/245.2 R |

FOREIGN PATENT DOCUMENTS

| | | |
|---|---|---|
| 227881 | 7/1962 | Austria . |
| 0013617 | 7/1980 | European Pat. Off. . |
| 0013662 | 7/1980 | European Pat. Off. . |
| 2047684A | 12/1980 | United Kingdom . |

OTHER PUBLICATIONS

JCS, Chemical Communications, No. 21, Nov. 1, 1979, pp. 962–963.
Johansson, Acta Chemica Scandinavica, B 30, (1976), 377–382.

Primary Examiner—Nicholas S. Rizzo
Attorney, Agent, or Firm—Cushman, Darby & Cushman

[57] ABSTRACT

This invention relates to penicillanic acid derivatives of the formula I

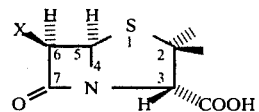

in which X stands for chlorine, bromine or iodine, to pharmaceutically acceptable, non-toxic salts of the compounds of formula I, to pharmaceutically acceptable, easily hydrolyzable esters thereof, including salts of such esters, to pharmaceutical compositions containing the compounds of the invention and dosage units thereof, to methods for the preparation of the compounds of the invention, and to methods of using the said new compounds in the human and veterinary therapy.

The 6β-halopenicillanic acids of formula I are potent inhibitors of β-lactamases from a variety of gram-positive and gram-negative bacteria, making the 6β-halopenicillanic acids as well as their salts and easily hydrolyzable esters valuable in human and veterinary medicine.

1 Claim, No Drawings

SUBSTANTIALLY PURE DICYCLOHEXYL AMMONIUM 6-β-BROMO-PENICILLANATE

This invention relates to penicillanic acid derivatives of the formula I

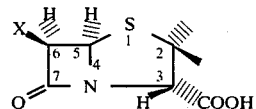

in which X stands for chlorine, bromine or iodine, to pharmaceutically acceptable, non-toxic salts of the compounds of formula I, to pharmaceutically acceptable, easily hydrolyzable esters thereof, including salts of such esters, to pharmaceutical compositions containing the compounds of the invention and dosage units thereof, to methods for the preparation of the compounds of the invention, and to methods of using the said new compounds in the human and veterinary therapy.

In the treatment of bacterial infections it is a serious problem that β-lactamase producing bacteria are occurring with increasing frequency. These enzymes inactivate a variety of β-lactam antibiotics, and it is well recognized that β-lactamases from both gram-positive and gram-negative bacteria contribute significantly to the resistance of bacteria to β-lactam antibiotics.

It has now been found that the 6β-halopenicillanic acids of formula I are potent inhibitors of β-lactamases from a variety of gram-positive and gram-negative bacteria. This property makes the 6β-halopenicillanic acids as well as their salts and easily hydrolyzable esters valuable in human and veterinary medicine because they can protect β-lactam antibiotics against inactivation when co-administered with these.

In addition to the inhibitory activity against β-lactamases, the 6β-halopenicillanic acids have antibacterial properties (cf. Table I) and are particularly active against Neisseria species.

Apart from 6β-bromopenicillanic acid, which has been mentioned in the literature (see below), the compounds of the invention are new, and none of them, including 6β-bromopenicillanic acid, have hitherto been obtained in a pure state.

It has been reported (J. Org. Chem. Vol. 43, pp. 3611–3613, 1978; Proc. Natl. Acad. Sci. USA, Vol. 75, pp. 4145–4149, 1978; U.S. Pat. No. 4,180,506 (Dec. 25, 1979); Biochem. J., Vol. 177, pp. 365–367, 1979) that mixtures of 6β- and 6α-bromopenicillanic acids are obtained either on epimerization of the latter or by selective hydrogenation of 6,6-dibromopenicilllanic acid, the 6β-bromo epimer being present in the reaction mixtures in estimated amounts of from 5 to 15%. The same literature has reported that such epimeric mixtures act as inhibitors of β-lactamases, and since pure 6α-bromopenicillanic acid has no effect on these enzymes, the inhibitory activity has been attributed to the 6β-bromo isomer. After the submission of the priority document corresponding to the present application, it has been reported (Tetrahedron Letters No. 48, pp. 4631–4634, Nov. 1979) that selective reduction of trimethylsilyl 6,6-dibromopenicillanate with tri-n-butyltin hydride followed by hydrolysis and salt formation afforded a 30 percent yield of sodium 6β-bromopenicillanate containing less than 5 percent of the 6α-bromo epimer, but that the major side reaction was overreduction to penicillanic acid. The same literature also describes a similar reduction of the corresponding 6-chloro-6-iodopenicillanate providing a 39 percent yield of a mixture of 6β- and 6α-chloropenicillanic acids containing about 25 percent of the 6α-epimer. However, neither 6β-bromo- and 6β-chloropenicillanic acid nor salts and easily hydrolyzable esters of these compounds have so far been isolated in a pure crystalline state. 6β-Iodopenicillanic acid or its salts and esters have not been reported previously in the literature.

Thus, it is one object of the present invention to provide 6β-halopenicillanic acids of the formula I and salts thereof in an essentially pure, crystalline form, suitable for medical use, these compounds exhibiting strong β-lactamase inhibitory activity increasing in the order Cl < Br < I and also showing antibacterial activity, in particular against Neisseria species.

Another object of the present invention is to provide easily hydrolyzable esters of the acids of formula I and salts of such esters being useful as pro-drugs and/or intermediates.

It is a further object of the invention to provide combinations of the compounds of the invention with selected β-lactam antibiotics, with which the new compounds act synergistically against a variety of β-lactamase producing bacteria because they protect the β-lactam antibiotics against inactivation by these enzymes.

Other objectives of the present invention will be apparent from the following description.

The salts of the 6β-halopenicillanic acids are salts with pharmaceutically acceptable, non-toxic bases, and among the suitable salts mention may be made of alkali metal salts and alkaline earth metal salts, such as lithium, sodium, potassium, magnesium, and calcium salts, as well as salts with ammonia and suitable non-toxic amines, such as lower alkylamines, e.g. triethylamine, lower alkanolamines, e.g. diethanolamine or triethanolamine, procaine, cycloalkylamines, e.g. dicyclohexylamine, benzylamines, e.g. N-methylbenzylamine, N-ethylbenzylamine, N-benzyl-β-phenethylamine, N,N'-dibenzylethylenediamine or dibenzylamine, and heterocyclic amines, e.g. morpholine, N-ethylpiperidine or the like. Also salts formed with e.g. β-lactam antibiotics or pro-drugs thereof containing a basic group, such as pivampicillin, pivmecillinam, bacampicillin, bacmecillinam, penethamate, ampicillin or amoxycillin, are within the scope of the invention. In some instances, it is preferred to use salts which are readily soluble in water, whereas for other purposes, it may be appropriate to use an only slightly soluble salt, e.g. in order to obtain a prolonged effect or for preparation of aqueous suspensions.

The above list shall, however, only be considered illustrative for and not limiting the present invention.

The present esters of the 6β-halopenicillanic acids are esters which are readily hydrolyzed in vivo or in vitro. Such esters include acyloxyalkyl, alkoxycarbonyloxyalkyl or aminoacyloxyalkyl esters of the formula II

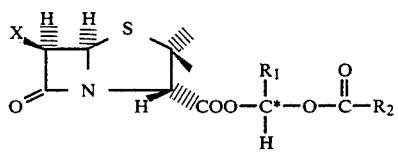

in which X has the same meaning as in formula I. $R_1$ is hydrogen, methyl or ethyl, and $R_2$ is a straight or branched alkyl or alkoxy with from 1 to 6 carbon atoms, or an aryl or aryloxy radical, or $R_2$ is a straight or branched aminoalkyl radical with from 1 to 6 carbon atoms, the alkyl moiety optionally being substituted by one or more additional groups, such as hydroxy, mercapto, alkoxy, alkylthio, carbalkoxy, carboxamido, phenyl or hydroxyphenyl. The asterisk in the ester moiety indicates the possibility of an asymmetric carbon atom.

Among the above esters the following are preferred: alkanoyloxymethyl with from 3 to 8 carbon atoms, 1-(alkanoyloxy)ethyl with from 4 to 9 carbon atoms, alkoxycarbonyloxymethyl with from 3 to 6 carbon atoms, 1-(alkoxycarbonyloxy)ethyl with from 4 to 7 carbon atoms, and α-aminoalkanoyloxymethyl with from 2 to 6 carbon atoms.

Other preferred esters are lactonyl esters, e.g. 3-phthalidyl, 4-crotonolactonyl or γ-butyrolacton-4-yl esters.

Also within the scope of the invention are methoxymethyl, cyanomethyl, or mono- or dialkyl substituted aminoalkyl esters, e.g. 2-dimethylaminoethyl, 2-diethylaminoethyl, or 3-dimethylaminopropyl esters.

In particular, such esters are preferred which are well-absorbed upon oral administration and during or after the absorption are hydrolysed to the free acids of formula I.

Esters which contain an amino group in the ester moiety can be prepared and used in the form of their salts with pharmaceutically acceptable, non-toxic inorganic or organic acids. Examples of suitable inorganic and organic acids include, but are not limited to, the following: hydrohalide acids, e.g. hydrochloric, hydrobromic and hydriodic acid, phosphoric acid, sulphuric acid, nitric acid, p-toluenesulphonic acid, methanesulphonic acid, formic acid, acetic acid, propionic acid, citric acid, tartaric acid, maleic acid, pamoic acid, p-(dipropylsulfamyl)benzoic acid (probenecid), and phenoxymethylpenicillin or other acidic β-lactam antibiotics. As mentioned above, easily soluble or only slightly soluble salts may be preferred for different purposes.

The present invention also relates to methods for the preparation of the compounds of the invention including their separation from mixtures containing the corresponding 6α-epimers and/or 6,6-dihalo derivatives which may be present in the crude reaction mixtures.

According to one method, mixtures of epimeric 6-halopenicillanic acids are produced by aqueous equilibration of a salt of a 6α-halopenicillanic acid at 30°–40° C. and a moderately basic pH-value (8–10) for 6–48 hours, preferably at 30°–32° C. and pH 9.0–9.1 for 20–24 hours, the pH in the reaction mixture being held constant by addition of dilute aqueous base via an automatic titrator. The amount of 6β-halo epimer present in the resulting mixtures decreases in the order I>Br>Cl, but the yields of the β-epimers are at least twice as high as those described in the literature for the epimerization of 6α-bromopenicillanic acid or by using said method for the epimerization of the corresponding 6α-chloro and 6α-iodo acids.

The epimeric mixtures of 6-chloro-, 6-bromo-, or 6-iodopenicillanic acids thus obtained can be separated by column chromatography on silica gel using as developing solvent an appropriate mixture of organic solvents, e.g. ether-petroleum ether, ethyl acetate-petroleum ether, chloroform-benzene or ethyl acetate-cyclohexane, these solvent mixtures preferably containing a low percentage (0.1–0.5%) of a carboxylic acid, such as formic acid or acetic acid. A highly efficient developing solvent for the separation of the epimeric mixtures referred to above by dry column chromatography on silica gel is e.g. ether-petroleum ether-formic acid, 70:30:0.1. Hereby the more polar 6β-halopenicillanic acids are completely separated from their less polar 6α-epimers and, following a usual work-up procedure of the eluates, obtained in a pure crystalline state, either in the form of the free acids or as the corresponding potassium or sodium salts. The purity of the crystalline 6β-halopenicillanic acids thus obtained as well as the respective potassium and sodium salts is at least 99 percent, as determined by thin-layer and gas-liquid chromatography.

In another embodiment of the method 6,6-dihalopenicillanic acids or salts thereof can be selectively reduced by treatment with alkali metal or tetraalkylammonium boranates, e.g. sodium borohydride, potassium borohydride, sodium cyanoborohydride, tetrabutylammonium boranate, or cetyl trimethylammonium boranate to afford favourably high yields (>50%) of the free 6β-halopenicillanic acids of formula I. The reactions are performed in an appropriate organic solvent, e.g. dimethyl sulphoxide, dimethylformamide, ethyl acetate or methylene chloride, and at temperatures between 0° and 80° C., preferably at room temperature. The 6β-halopenicillanic acids of formula I can be separated from the corresponding 6α-halo- and/or 6,6-dihalopenicillanic acids present in the crude reaction mixtures by column chromatography as referred to above or by fractionate crystallization known to the man skilled in the art.

According to a further aspect of the present invention, the new esters of the 6β-halo acids of formula I can be prepared by epimerization of the corresponding 6α-halopenicillanic acid esters in an appropriate organic solvent, e.g. methylene chloride, chloroform or dimethylformamide, in the presence of an organic base, e.g. 1,5-diazabicyclo[4.3.0]non-5-ene or triethylamine, and at temperatures between −10° C. and room temperature. The epimeric mixtures of the corresponding 6-halopenicillanic acid esters thus obtained are separated by column chromatography under similar conditions as mentioned above to afford the pure 6β-halo isomers.

In a further embodiment of the method, the esters of the present invention can be obtained by selective reduction of 6,6-dihalopenicillanic acid esters with alkali metal or tetraalkylammonium boranates, similar to the procedure referred to before. The 6β-halo esters thus obtained are separated from minor amounts of the corresponding 6α-epimers and/or unreacted starting materials by column chromatography as described above.

The 6β-halopenicillanic acids of formula I or their salts can be converted into the corresponding esters by well known esterification processes, and vice versa such esters can be cleaved chemically or enzymatically to give the corresponding free acids of formula I or salts thereof under conditions which do not result in any appreciable destruction of the remaining part of the molecule.

As it has been previously stated, the 6β-halopenicillanic acids of the present invention are potentiators of β-lactamase sensitive antibiotics and may by themselves be useful in combatting some specific bacterial infections.

More specifically, the antibacterial spectra of the pure 6β-halopenicillanic acids of the invention will appear from Table I below.

TABLE I

Antibacterial spectra[a] of 6β-bromopenicillanic acid (A), 6β-chloropenicillanic acid (B) and 6β-iodopenicillanic acid (C)

| Organism | IC$_{50}$ (μg/ml) | | |
|---|---|---|---|
| | A | B | C |
| Staph. aureus CJ9 | 32 | 40 | 63 |
| Dipl. pneumoniae EA | 1.6 | 5.0 | 5.0 |
| Strep. pyogenes EC | 6.3 | 6.3 | 5.0 |
| Strep. faecalis EI3 | >100 | >100 | >100 |
| Coryneb. xerosis FF | 5.0 | 5.0 | 16 |
| Bacillus subt. KA2 | 5.0 | 7.9 | 13 |
| Pseud. aeruginosa BA2 | >100 | >100 | >100 |
| Alcaligenes faecalis GA | 2.0 | 2.5 | 10 |
| Escherichia coli HA2 | 50 | 50 | >100 |
| Escherichia coli HA58(RTEM) | 100 | >100 | >100 |
| Kleb. pneumoniae HE | 63 | 63 | >100 |
| Enterobact. aerogenes HC7A | 63 | 63 | >100 |
| Proteus vulg. HJ | 40 | 40 | 100 |
| Salm. typhimurium HL2 | 100 | 100 | >100 |
| Shigella dysenteriae HR | 50 | 40 | >100 |
| Neisseria gonorrhoeae DA2 | 0.25 | 0.20 | 0.79 |
| Neisseria meningitidis DB | 0.79 | 0.63 | 1.6 |
| Haemophilus influenzae IX3 | 32 | 20 | >100 |

[a]Determined by serial dilutions in fluid medium, inoculum 10$^6$ CFU[b] (gram-positive organism) or 10$^4$ CFU (gram-negative organism)
[b]CFU = colony forming units In Table II is shown the in vitro activity against β-lactamase producing bacterial strains of selected β-lactam antibiotics in 1:1 combinations with the 6β-halopenicillanic acids of formula I. These data indicate that, in combination with the 6β-halopenicillanic acids, benzylpenicillin and ampicillin are highly active against otherwise resistant strains of Staphylococcus aureus. A similar synergistic effect against strains of Klebsiella pneumoniae, Proteus mirabilis, and Escherichia coli is shown by combinations of ampicillin as well as mecillinam with the 6β-halo acids of the invention.

for the treatment of infections in mammals including humans.

The free 6β-halopenicillanic acids of formula I or their salts may be used for enteral, parenteral and topical administration. However, for oral use it may in some instances be advantageous to use an easily hydrolyzable ester of the invention or a salt thereof.

Injectable or infusable compositions of the 6β-halopenicillanic acids of formula I or their salts are suitable, when high tissue levels of the 6β-halopenicillanic acids are rapidly desired, or when used in combination with a parenterally administered β-lactam antibiotic, as described below.

For intramammal use it is preferred to use an ester of the invention which provides an adequate local concentration, e.g. a dialkylaminoalkyl ester or a salt thereof.

The active ingredient can be used as such or can be mixed up with carriers and/or auxiliary agents.

In such compositions, the proportion of therapeutically active material to carriers and auxiliary agents can vary between 1% and 95%. The compositions can be worked up to pharmaceutical forms of presentation such as tablets, capsules, powders, syrups, suspensions, solutions, including forms suitable for injection or infusion.

The carriers and/or auxiliary agents are pharmaceutically acceptable materials such as gelatine, lactose, starch, magnesium stearate, talc, vegetable and animal fats and oils, gum, polyalkylene, glycol, or other known carriers for medicaments, and diluents, binders, buffers, preservatives, disintegrants, coating materials, and the like in accordance with pharmaceutical practice in the manner well understood by those skilled in the art, in order to provide appropriate forms of pharmaceutical presentation, including sustained release preparations, double tablets containing the therapeutically active ingredients separated from each other, and enteric coated tablets, etc.

TABLE II

Susceptibility[a] of β-lactamase producing bacterial strains to selected β-lactam antibiotics in 1:1 combinations with 6β-bromopenicillanic acid (A), 6β-chloropenicillanic acid (B), and 6β-iodopenicillanic acid (C)

| Antibiotic | IC$_{50}$ (μg/ml) | | | | |
|---|---|---|---|---|---|
| | Staphylococcus aureus CJ9 | Staphylococcus aureus CJ145 | Klebsiella pneumoniae HE7 | Proteus mirabilis HJ28 | Escherischia coli HA58 (RTEM) |
| A | 13 | 10 | >50 | >50 | >50 |
| B | 16 | 13 | >50 | >50 | >50 |
| C | 20 | 6.3 | >100 | >100 | >100 |
| Benzylpenicillin | >100 | 10 | >100 | >100 | >100 |
| Benzylpenicillin + A | 0.5 + 0.5 | 0.2 + 0.2 | ND[b] | ND | ND |
| Benzylpenicillin + B | 1.3 + 1.3 | 0.4 + 0.4 | ND | ND | ND |
| Benzylpenicillin + C | 0.79 + 0.79 | 0.08 + 0.08 | 7.9 + 7.9 | 2.5 + 2.5 | 7.9 + 7.9 |
| Ampicillin | 10 | 1.6 | >50 | >50 | >100 |
| Ampicillin + A | 0.4 + 0.4 | 0.16 + 0.16 | 1.3 + 1.3 | 5.0 + 5.0 | 4.0 + 4.0 |
| Ampicillin + B | 1.6 + 1.6 | 0.32 + 0.32 | ND | ND | ND |
| Ampicillin + C | 0.79 + 0.79 | 0.16 + 0.16 | 2.5 + 2.5 | 2.5 + 2.5 | 3.2 + 3.2 |
| Mecillinam | >50 | >50 | >25 | 6.3 | 1.3 |
| Mecillinam + A | 4.0 + 4.0 | 3.2 + 3.2 | 5.0 + 5.0 | 1.3 + 1.3 | 0.16 + 0.16 |
| Mecillinam + B | ND | 4.0 + 4.0 | ND | ND | 0.05 + 0.05[c] |
| Mecillinam + C | 10 + 10 | 3.2 + 3.2 | 0.79 + 0.79 | 0.63 + 0.63 | 0.13 + 0.13 |

[a]Serial dilutions in agar medium, inoculum 10$^5$ CFU (gram-positive organisms) or 10$^4$ CFU (gram-negative organisms)
[b]ND = not determined
[c]Corresponding to an IC$_{50}$ of 0.4 μg/ml for mecillinam in this test It is also an object of the present invention to provide pharmaceutical compositions for use in the treatment of infectious diseases which contain as an active ingredient at least one of the compounds of the invention.

The compositions include forms adapted for enteral, parenteral, intramammal or topical use and may be used The compounds of the invention may be present in the composition as the sole agent or together with other therapeutic agents, in particular a β-lactam antibiotic or a synergistic combination of β-lactam antibiotics. Suitable β-lactam antibiotics for such compositions include not only those known to be highly susceptible to β-lactamases, but also those which have a good degree of intrinsic resistance to β-lactamases. Thus, suitable β-lactam antibiotics for such compositions include benzylpenicillin, phenoxymethylpenicillin, carbenicillin, methicillin, propicillin, ampicillin, amoxycillin, epicillin, ticarcillin, cyclacillin, cephaloridine, cephalothin, cefazolin, cephalexin, cefaclor, cephacetrile, cephamandole, cephapirin, cephradine, cephaloglycine, mecillinam, and other well known penicillins, cephalosporins or amidinopenicillanic acids or pro-drugs thereof, such as hetacillin, metampicillin, the acetoxymethyl, pivaloyloxymethyl, ethoxycarbonyloxyethyl, and phthalidyl esters of benzylpenicillin, ampicillin, amoxycillin or cephaloglycine, or the phenyl, tolyl, and indanyl α-esters of carbenicillin, ticarcillin or the like, or 6β-amidinopenicillanic acid pro-drugs, like pivmecillinam or bacmecillinam, or a similar 7β-amidinocephalosporanic acid derivative.

When present in a pharmaceutical composition together with another β-lactam antibiotic, the ratio of the compounds of the invention to the other β-lactam antibiotic(s) is from 10:1 to 1:10 and advantageously may be from 3:1 to 1:3, calculated as the free acids, the range, however, not to be considered limiting the invention.

Another object of the invention resides in the selection of a dose of the compounds of the invention and a dosage unit of the compositions of the invention which dose and dosage unit can be administered so that the desired results are achieved without simultaneous secondary effects.

The compositions of the invention are conveniently administered in dosage units containing a total amount of from 0.025 g to 2.5 g, and preferably from 0.1 g to 1.0 g, of the antibacterial agents, calculated as the free acids. The expression "antibacterial agents" shall here and in the following mean one or more compounds of the invention, alone or combined with one or more known β-lactam antibiotics, salts or pro-drugs thereof. When used in the veterinary practice, the dosage units may contain up to 25 g of the antibacterial agents.

By the term "dosage unit" is meant a unitary, e.g. a single dose capable of being administered to a patient, and which may be readily handled and packed, remaining as a physically stable unit dose, comprising either the active materials as such or a mixture thereof with a pharmaceutical carrier.

Similarly, for infusion, the compositions of the invention are given in dosage units containing up to 10 g of the antibacterial agents in aqueous solution.

For parenteral use, e.g. injections, the compositions of the invention are given e.g. in an aqueous solution or suspension as a dosage unit containing from 0.1 g to 1 g of the antibacterial agents, calculated as the free acids, to be dissolved or suspended immediately before use, or ready for use together with a pharmaceutically acceptable vehicle.

In the form of a dosage unit the compounds may be administered once or more times a day at appropriate intervals, always depending, however, on the condition of the patient.

Thus, a daily dose will amount to from 0.1 g to 30 g (corresponding to 1–425 mg/kg body weight/day), preferably from 0.2 g to 6 g of the antibacterial agents, calculated as the free acids.

The compositions of the invention may be used in the treatment of infections of inter alia the respiratory tract, the urinary tract, and soft tissues in humans and may also be used to treat infections in animals such as mastitis in cattle.

In compounded compositions containing other β-lactam antibiotics, the latter will normally be present in approximately the same amounts as conventionally used when such β-lactam antibiotics are the sole therapeutic agents, but under certain circumstances it may be appropriate to reduce the amounts thereof.

Particularly favoured compounded compositions will contain from 50–1000 mg of the β-lactam antibiotic, a salt or a pro-drug thereof, and the 6β-halopenicillanic acid, a salt or a pro-drug thereof, in an amount within the aforementioned ratios, and more suitably from 200–500 mg of the β-lactam antibiotic, a salt or a pro-drug thereof, and from 25–250 mg of the 6β-halopenicillanic acid, a salt or a pro-drug thereof.

The compounds of the invention may be administered in the form of their pharmaceutically acceptable, non-toxic esters. The term "non-toxic" for such esters means that they are therapeutically acceptable for their intended form of administration. In general, the esters of the compounds of the invention are used in the oral administration, but their use in the parenteral administration is also within the scope of the invention.

The present invention also comprises a method for the treatment of humans and other mammals, consisting in the administration of an effective amount of the present compositions to patients suffering from infectious diseases.

The method may consist in administering compositions or compounded compositions of the invention, or in administering such compositions containing the compounds of the invention alone together with compositions containing other β-lactam antibiotics. In the latter case, the two types of compositions may be administered simultaneously or at intervals and with varying proportions between the 6β-halopenicillanic acid and the β-lactam antibiotic.

According to the invention between 0.1 and 30 g of the antibacterial agents will be administered each day of the treatment, but more often between 500 and 6000 mg of the antibacterial agents will be administered per day.

It shall be expressly understood that the above ranges of doses indicate the total amount of antibacterial agents, i.e. one or more compounds of the invention administered either alone, combined with, or given at intervals with other β-lactam antibiotics as above.

The invention will be further described in the following Examples which are not to be construed as limiting the invention.

EXAMPLE 1

Potassium 6β-bromopenicillanate

A solution of potassium 6α-bromopenicillanate (7.64 g, 24 mmol) in 0.04M aqueous disodium hydrogen phosphate (800 ml) was incubated for 72 hours at 30° C. According to an NMR-spectrum ($D_2O$) of a freeze-dried 5 ml sample, the epimeric mixture contained 10–12% of the 6β-bromo compound.

After addition of sodium chloride (160 g), the mixture was stirred at 0° C. under a layer of ether (250 ml), and the pH of the aqueous phase was adjusted to 3 with 4N aqueous hydrochloride. The organic layer was separated, the aqueous phase was re-extracted with ether (100 ml), and the combined ethereal extracts were washed with saturated aqueous sodium chloride (10 ml), dried, and concentrated to about 40 ml at reduced pressure. The concentrated solution was subjected to dry column chromatography on silica gel (Silica Woelm TSC, Woelm Pharma, Eschwege, Western Germany). The column ($\phi$ 5.6 cm, length 46 cm) was developed with ether-petroleum ether-formic acid, 70:30:0.1 (1200 ml), fractions á 2 cm were scraped out, suspended in ethyl acetate (10 ml/fraction), and samples of the supernatants were examined by thin-layer chromatography using the above mentioned solvent system. Fractions containing the pure, more polar 6$\beta$-bromopenicillanic acid were combined and eluted with ethyl acetate. The resulting ethyl acetate eluate was concentrated to about 50 ml at reduced pressure and washed thoroughly with water (6×5 ml) to remove the major amount of formic acid. To the organic layer was added water (40 ml), and the apparent pH of the mixture was adjusted to 7.2 by addition of 0.5M aqueous potassium bicarbonate. The aqueous layer was separated and freeze-dried to afford 0.54 g of pure potassium 6$\beta$-bromopenicillanate as a colourless amorphous powder which crystallized from n-butanol, $[\alpha]_D^{20}+240°$ (c=0.2, H$_2$O).

The detailed FT proton NMR-spectrum showed signals at $\delta$=1.47 (s, 3H; CH$_3$-2$\alpha$), 1.59 (s, 3H; CH$_3$-2$\beta$), 4.27 (s, 1H; CH-3), 5.52 and 5.58 (doublets, J=4 Hz, 2H; CH-5$\alpha$ and CH-6$\alpha$) ppm.

Instrument JEOL FX 100. Concentration 50 mg per ml. All data converted to tetramethylsilane as 0.00 ppm $\delta$-scale.

EXAMPLE 2

Potassium 6$\beta$-chloropenicillanate

A solution of potassium 6$\alpha$-chloropenicillanate (13.14 g, 48 mmol) in 0.04M aqueous disodium hydrogen phosphate (1600 ml) was incubated for 96 hours at 30° C. to yield, as revealed by an NMR-spectrum (D$_2$O) of a freeze-dried 5 ml sample of the reaction mixture, about 5-6% of 6$\beta$-chloropenicillanic acid in admixture with the starting material.

To the reaction mixture was added sodium chloride (320 g) and ether (400 ml), and the pH of the aqueous phase was adjusted to 3 by addition of 4N aqueous hydrochloric acid at 0° C. with stirring. The organic phase was separated, the aqueous layer was re-extracted with ether (200 ml), and the combined ethereal extracts were washed with saturated aqueous sodium chloride (20 ml), dried, and concentrated to about 50 ml at reduced pressure. The concentrate was subjected to dry column chromatography on silica gel (as described in Example 1 for the separation of the corresponding 6-epimeric bromopenicillanic acids). Fractions containing the pure 6$\beta$-chloropenicillanic acid were eluted with ethyl acetate, and the resulting solution was worked up in a similar manner as described in Example 1 to afford 0.68 g of potassium 6$\beta$-chloropenicillanate as an amorphous powder which crystallized from n-butanol.

The NMR-spectrum (D$_2$O) showed signals at $\delta$=1.48 (s, 3H; CH$_3$-2$\alpha$), 1.58 (s, 3H; CH$_3$-2$\beta$), 4.27 (s, 1H, CH-3), 5.43 and 5.63 (2d, J=4 Hz, 2H; CH-5$\alpha$ and CH-6$\alpha$) ppm. Tetramethylsilane was used as external reference.

EXAMPLE 3

Potassium 6$\beta$-iodopenicillanate

By following the procedure of Example 1, but substituting potassium 6$\alpha$-iodopenicillanate for the potassium 6$\alpha$-bromopenicillanate, the desired compound was obtained as an amorphous product which crystallized from n-butanol.

EXAMPLE 4

Potassium 6$\beta$-bromopenicillanate

A solution of potassium 6$\alpha$-bromopenicillanate (15.28 g, 48 mmol) in water (320 ml) was adjusted to pH 9.0 with 1N aqueous sodium hydroxide and stirred for 24 hours at 30° C. During the reaction a pH of 9.0 was maintained in the solution by addition of 1N aqueous sodium hydroxide via an automatic titrator. An NMR spectrum (D$_2$O) obtained from a freeze-dried 1 ml sample of the solution indicated the presence of approximately 25% of the 6$\beta$-bromo compound in the epimeric mixture formed.

The mixture was worked up and purified by column chromatography as described in Example 1 to yield crystalline potassium 6$\beta$-bromopenicillanate identical with the product prepared in Example 1; $[\alpha]_D^{20}+253°$ (c=0.5, 1M phosphate buffer, pH 7).

Calculated for C$_8$H$_9$BrKNO$_3$S: C, 30.19; H, 2.85; Br, 25.11; N, 4.40; S, 10.08%. Found: C, 30.16; H, 2.95; Br, 25.28; N, 4.33; S, 10.07%.

EXAMPLE 5

Potassium 6$\beta$-chloropenicillanate

By following the procedure of Example 4, but substituting potassium 6$\alpha$-chloropenicillanate for the potassium 6$\alpha$-bromopenicillanate, an epimeric mixture containing about 15% of the 6$\beta$-chloro compound was obtained, as revealed by an NMR spectrum (D$_2$O) of a freeze-dried sample of the reaction mixture.

The crystalline title compound was obtained using a similar work-up and chromatography method as described in Example 1; $[\alpha]_D^{20}+243°$ (c=0.5, 1M phosphate buffer pH 7).

EXAMPLE 6

Potassium 6$\beta$-iodopenicillanate

A. Acetoxymethyl 6-diazopenicillanate

To a stirred solution of acetoxymethyl 6$\beta$-aminopenicillanate (5.77 g, 20 mmol) and sodium nitrite (2.76 g, 40 mmol) in a mixture of dichloromethane (120 ml) and water (120 ml) was added dropwise at 0°–3° C. 4N aqueous sulphuric acid (7 ml).

After stirring at the low temperature for a further 30 minutes, the organic phase was separated, dried (Na$_2$SO$_4$), and concentrated to approximately 30 ml at reduced pressure.

This concentrate was used immediately in the following step.

B. Acetoxymethyl 6$\alpha$-iodopenicillanate

The concentrated solution of acetoxymethyl 6-diazopenicillanate from step A above was diluted with icecold acetone (180 ml), and to the stirred mixture was added dropwise at 0°–3° C. a solution of sodium iodide (9.0 g, 60 mmol) and 57% hydroiodic acid (7.4 ml) in water (15 ml). After stirring at 0°–3° C. for a further 25 minutes, the mixture was treated with solid sodium bicarbonate (10 g) and filtered. The filtrate was diluted with ethyl acetate (150 ml), acetone was removed at reduced pressure, and the remaining organic layer was separated, washed with 0.5M aqueous sodium thiosulphate (2×100 ml), dried (Na$_2$SO$_4$), and concentrated to about 10 ml at reduced pressure.

This concentrated solution was subjected to dry column chromatography on silica gel (ether-petroleum ether, 4:6) to yield pure acetoxymethyl 6$\alpha$-iodopenicillanate as a slightly yellowish oil.

The NMR spectrum (CDCl$_3$) showed signals at δ=1.48 (s, 3H; CH$_3$-2α), 1.63 (s, 3H; CH$_3$-2β), 2.11 (s, 3H; COCH$_3$), 4.56 (s, 1H; CH-3), 4.99 (d, J=1.5 Hz, 1H; CH-6), 5.45 (d, J=1.5 Hz, 1H; CH-5), and 5.79 (ABq, J=5.5 Hz, 2H; OCH$_2$O) ppm.

Tetramethylsilane was used as internal reference.

C. Potassium 6α-iodopenicillanate

To a solution of acetoxymethyl 6α-iodopenicillante (2.0 g, 5 mmol) in 70% aqueous methanol (50 ml) was added 4N aqueous hydrochloric acid (1.5 ml), and, after protection from light, the mixture was stirred at room temperature for 3 days. The mixture was poured into water (150 ml), extracted twice with ether (100 ml), and the combined ethereal extracts were washed with water (2×25 ml). To the organic layer was added fresh water (40 ml), and the pH in the aqueous phase was adjusted to 6.8 by addition of 1M potassium bicarbonate with stirring. The aqueous phase was separated and freeze-dried to give potassium (6α-iodopenicillanate as an amorphous powder, which crystallized from acetone.

The NMR-spectrum (D$_2$O) showed signals at δ=1.46 (s, 3H; CH$_3$-2α), 1.57 (s, 3H; CH$_3$-2β), 4.30 (s, 1H; CH-3), 5.24 (d, J=1.5 Hz, 1H; CH-6), and 5.46 (d, J=1.5 Hz, 1H; CH-5) ppm.

D. Potassium 6β-iodopenicillanate

A solution of potassium 6α-iodopenicillanate (3.65 g, 10 mmol) in water (200 ml) was stirred at 30° C. for 20 hours, a constant pH of 9.0 being maintained in the reaction mixture by additions of 0.1N sodium hydroxide via an automatic titrator. According to the NMR spectrum (D$_2$O) of a freeze-dried 1 ml-sample, the epimeric mixture of 6-iodopenicillanates thus formed contained approximately 30% of the 6β-iodo compound.

To the mixture was added ether (150 ml), and the pH of the aqueous phase was adjusted to 3.0 by addition of 4N hydrochloric acid with stirring. The organic phase was separated, the aqueous phase re-extracted with ether (50 ml), and the combined ethereal extracts were washed with saturated aqueous sodium chloride (2×20 ml), dried (MgSO$_4$), and concentrated to about 6–8 ml at reduced pressure. The concentrate thus obtained was subjected to dry column chromatography on silica gel (ether-petroleum ether-formic acid, 70:30:0.1), and, analogously to the procedure described in Example 1 for the separation and isolation of the corresponding 6β- and 6α-bromo compounds, potassium 6β-iodopenicillanate was obtained in a crystalline state; $[α]_D^{20}$ +260° (c=0.5, 1M phosphate buffer pH 7).

The NMR spectrum (D$_2$O) showed signals at δ=1.49 (s, 3H; CH$_3$-2α), 1.65 (s, 3H; CH$_3$-2β), 4.29 (s, 1H; CH-3), 5.42 and 5.80 (2d, J=3.5 Hz, 2H; CH-5, and CH-6) ppm.

Calculated for C$_8$H$_9$IKNO$_3$S: C, 26.31; H, 2.48; I, 34.75; N, 3.84; S, 8.78%. Found: C, 26.51; H, 2.58; I, 34.91; N, 3.75; S, 8.80%.

EXAMPLE 7

Pivaloyloxymethyl 6β-bromopenicillanate

To a solution of potassium 6β-bromopenicillanate (0.64 g, 2 mmol) in dimethylformamide (15 ml) was added chloromethyl pivalate (0.27 ml, 2.5 mmol), and the mixture was stirred for 16 hours at room temperature. After dilution with ethyl acetate (45 ml), the mixture was washed with water (4×10 ml), dried (MgSO$_4$), and evaporated in vacuo. The residual oil crystallized from diisopropyl ether to give the title compound, melting point: 67°–68° C.

The NMR spectrum (CDCl$_3$) showed signals at δ=1.23 (s, 9H; C(CH$_3$)$_3$), 1.51 (s, 3H; CH$_3$-2α), 1.68 (s, 3H; CH$_3$-2β), 4.54 (s, 1H; CH-3), 5.32 and 5.57 (2d, J=4 Hz, 2H; CH-5 and CH-6), and 5.82 (ABq, J=5.5 Hz, 2H; OCH$_2$O) ppm. Tetramethylsilane was used as internal reference.

EXAMPLE 8

Pivaloyloxymethyl 6β-chloropenicillanate

By substituting potassium 6β-chloropenicillanate for the potassium 6β-bromopenicillanate in the procedure of Example 7, pivaloyloxymethyl 6β-chloropenicillanate was obtained as colourless crystals, melting point: 68°–69° C.

The NMR spectrum (CDCl$_3$) showed signals at δ=1.22 (s, 9H; C(CH$_3$)$_3$), 1.51 (s, 3H; CH$_3$-2α), 1.66 (s, 3H; CH$_3$-2β), 4.53 (s, 1H; CH-3), 5.22 and 5.60 (2d, J=4 Hz, 2H; CH-5 and CH-6), and 5.82 (ABq, J=5.5 Hz, 2H; OCH$_2$O) ppm. Tetramethylsilane was used as internal reference.

EXAMPLE 9

Pivaloyloxymethyl 6β-iodopenicillanate

A. Pivaloyloxymethyl 6-diazopenicillanate

A stirred mixture of pivaloyloxymethyl 6β-aminopenicillanate (3.30 g, 10 mmol) and sodium nitrite (1.38 g, 20 mmol) in methylene chloride (120 ml) and water (120 ml) was cooled to 0° C. and treated with 2N aqueous sulphuric acid (7.5 ml) for 40 minutes. The organic phase was separated, dried (Na$_2$SO$_4$), and concentrated at reduced pressure to about 30 ml. The concentrate was used immediately for the subsequent transformation.

B. Pivaloyloxymethyl 6α-iodopenicillanate

The concentrate of pivaloyloxymethyl 6-diazopenicillanate from step A above was diluted with acetone (120 ml), cooled to 0° C., and to the stirred mixture was added a cold solution of 67% aqueous hydroiodic acid (3.5 ml) and sodium iodide (4.5 g) in water (20 ml). After stirring for a further 20 minutes at the low temperature, the mixture was treated with solid sodium bicarbonate, filtered, and evaporated. The residue obtained was taken up in ethyl acetate (100 ml) and washed with 5% aqueous sodium thiosulphate (2×75 ml). The organic phase was separated, dried (MgSO$_4$), and evaporated in vacuo. The residual oil was purified by column chromatography on silica gel using ether-petroleum ether, 30:70, as the eluant to yield pure pivaloyloxymethyl 6α-iodopenicillanate as colourless crystals from diisopropyl ether, melting point: 63°–64° C.

C. Pivaloyloxymethyl 6β-iodopenicillanate

To a stirred solution of pivaloyloxymethyl 6α-iodopenicillanate (0.88 g, 2 mmol) in dry methylene chloride (20 ml) was added at −5° C. a 1M solution of 1,5-diazabicyclo[4.3.0]non-5-ene (DBN) in dry methylene chloride (2 ml). The mixture was stirred at 0° C. for 20 minutes, shaken with 1N aqueous acetic acid (2 ml), diluted with methylene chloride (20 ml), washed with water (2×10 ml), dried (Na$_2$SO$_4$), and evaporated in vacuo to a dark oil. The residue was purified by colomn chromatography on silica gel using ether-petroleum ether, 30:70, as the eluant to afford pivaloyloxymethyl 6β-iodopenicillanate as a slightly yellowish oil which crystallized from diisopropyl ether, melting point: 78°–79° C.

The NMR spectrum (CDCl$_3$) showed signals at δ=1.23 (s, 9H; C(CH$_3$)$_3$), 1.49 (s, 3H; CH-2α), 1.70 (s, 3H; C$\underline{H}_3$-2β), 4.55 (s, 1H; C$\underline{H}$-3), 5.38 and 5.62 (2d, J=4 Hz, 2$\underline{H}$; C$\underline{H}$-5 and C$\underline{H}$-6), and 5.81 (ABq, J=5.5 Hz, 2H; OC$\underline{H}_2$O) ppm. Tetramethylsilane was used as internal reference.

EXAMPLE 10

Acetoxymethyl 6β-bromopenicillanate

Chloromethyl acetate (0.11 ml, 1.2 mmol) was added to a solution of potassium 6β-bromopenicillanate (0.32 g, 1 mmol) in dimethylformamide (5 ml), and the mixture was stirred for 16 hours at room temperature in a dark room. After dilution with ether (20 ml), the mixture was washed with water (4×5 ml), dried (MgSO$_4$), and evaporated in vacuo to yield the title compound as a yellowish oil.

The NMR spectrum (CDCl$_3$) showed signals at δ=1.49 (s, 3H; C$\underline{H}_3$-2α), 1.68 (s, 3H; C$\underline{H}_3$-2β), 2.11 (s, 3H; COC$\underline{H}_3$), 4.54 (s, 1H; C$\underline{H}$-3), 5.33 and 5.59 (2d, J=4 Hz, 2H; C$\underline{H}$-5α and C$\underline{H}$-6α), and 5.82 (ABq, J=5.5 Hz, 2H; OC$\underline{H}_2$O) ppm. Tetramethylsilane was used as internal reference.

EXAMPLE 11

Acetoxymethyl 6β-iodopenicillanate

Following the procedure of Example 10, but substituting potassium 6β-iodopenicillanate for the potassium 6β-bromopenicillanate, the title compound was obtained as a yellowish oil.

The NMR spectrum (CDCl$_3$) showed signals at δ=1.50 (s, 3H; C$\underline{H}_3$-2α), 1.70 (s, 3H; C$\underline{H}_3$-2β), 2.12 (s, 3H; COC$\underline{H}_3$), 4.55 (s, 1H; C$\underline{H}$-3), 5.39 and 5.63 (2d, J=3.5 Hz, 2H; C$\underline{H}$-5α and C$\underline{H}$-6α), and 5.83 (ABq, J=5.5 Hz, 2H; OC$\underline{H}_2$O) ppm. Tetramethylsilane was used as internal reference.

EXAMPLES 12–14

6β-Halopenicillanic acids

The crystalline 6β-halopenicillanic acids listed in Table III below could be obtained as follows:

(a) By concentrations at reduced pressure of the ethyl acetate solutions containing the pure 6β-halo compounds obtained after separation from the corresponding 6α-epimers by dry column chromatography on silica gel (as described in Example 1).

(b) By liberation from aqueous solutions of the corresponding potassium salts under a layer of ether or ethyl acetate at pH 3 followed by separation of the organic phase, drying, and crystallization from ether-diisopropylether or ethyl acetate-hexane.

TABLE III

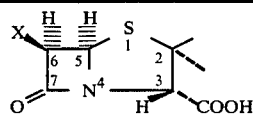

| Example | X | $[α]_D^{20}$ (c = 0.5, CHCl$_3$) | $^1$H—NMR data (δ/ppm; CD$_3$CN) C$\underline{H}$—5 and C$\underline{H}$—6 |
|---|---|---|---|
| 12 | Br | +272° | 5.48 and 5.54, 2d, J = 4.0 Hz |
| 13 | Cl | +264° | 5.38 and 5.58, 2d, J = 4.0 Hz |
| 14 | I | +276° | 5.35 and 5.74, 2d, J = 4.0 Hz |

The above acids decompose at about 80°–100° C., therefore a well-defined melting point cannot be determined.

EXAMPLE 15

Sodium 6β-bromopenicillanate

A. Tetrabutylammonium 6,6-dibromopenicillanate

To a solution of tetrabutylammonium hydrogen sulphate (34 g, 0.1 mol) in water (50 ml), methylene chloride (100 ml) was added, followed by 2N sodium hydroxide (50 ml). To the stirred mixture was added 6,6-dibromopenicillanic acid (36 g, 0.1 mol) and the pH adjusted to 7.0 with 2N sodium hydroxide. The organic layer was separated, and the aqueous phase was re-extracted with methylene chloride (50 ml). After drying of the combined organic phases, ethyl acetate (500 ml) was added, and the solution was concentrated to about 300 ml in vacuo.

B. Sodium 6β-bromopenicillanate

To the above solution of tetrabutylammonium 6,6-dibromopenicillanate, tetrabutylammonium boranate (24.9 g, 0.1 mol) was added in one portion with stirring. After about 30 minutes, the temperature in the mixture had raised to 45°–50° C., whereafter it slowly decreased. After standing for 1 hour, the solution was diluted with ether (300 ml), water (300 ml) was added, and the pH was adjusted to 3 with hydrochloric acid. The organic phase was separated and washed with water. Fresh water (50 ml) was added to the organic phase, and the pH was adjusted to 6.8 with aqueous potassium bicarbonate. The aqueous layer was separated, and water was removed azeotropically with n-butanol in vacuo to yield a crystalline mixture of the potassium salts of 6β-bromo-, 6α-bromo-, and 6,6-dibromopenicillanic acid in an approximate ratio of 65:25:10.

From an aqueous solution of the above salts, the free acids were liberated at pH 3 (dilute hydrochloric acid) under a layer of ether, and the resulting mixture was separated by column chromatography in a similar way as described in Example 1 to yield, after salt formation with 0.5M sodium bicarbonate and removal of water by azeotropic distillation with n-butanol, crystalline sodium 6β-bromopenicillanate; $[α]_D^{20}$+266° (c=0.5, 1M phosphate buffer pH 7).

Calculated for C$_8$H$_9$BrNNaO$_3$S: C, 31.80; H, 3.00; Br, 26.45; N, 4.64; S, 10.61%. Found: C, 31.85; H, 3.04; Br, 26.53; N, 4.56; S, 10.72%.

EXAMPLE 16

6β-Bromopenicillanic acid

To a stirred suspension of potassium 6,6-dibromopenicillanate (11.91 g, 30 mmol) in dimethylformamide (30 ml) was added sodium borohydride (1.14 g, 30 mmol). In the course of approximately 30 minutes, the temperature in the reaction mixture rose to about 50° C., whereafter it slowly decreased to normal. After stirring at room temperature for 20 hours, water (100 ml) and ether (100 ml) were added, and the pH of the mixture was adjusted to 3 with dilute hydrochloric acid. The organic layer was separated, the aqueous layer was extracted with ether (25 ml), and the combined organic extracts were washed with water (25 ml). To the organic phase was added fresh water (25 ml), and the pH of the aqueous phase was adjusted to 7 by addition of 1M potassium bicarbonate with stirring. The aqueous layer was separated, and the water removed azeotropically by distillation with n-butanol in vacuo to give a crystalline mixture of the potassium salts of 6β- and 6α-bromopenicillanic acid in an approximate ratio of 55:45, as indicated by NMR spectroscopy.

The above potassium salts were dissolved in water (5 ml/g salt), and the pH of the aqueous phase was adjusted to 3 with 4N hydrochloric acid under a layer of ethyl acetate 5 ml/g salt). The organic phase was separated, washed with water, dried, and diluted with an equal volume of hexane. Seeding of the resulting solution followed by concentration at reduced pressure to about half the volume afforded crystalline 6$\beta$-bromopenicillanic acid which was filtered off, washed with ethyl acetate-hexane (1:1), and dried. Recrystallization from ether-diisopropyl ether gave the analytical sample, $[\alpha]_D^{20}$ +268° (c=0.5, CHCl$_3$).

Calculated for C$_8$H$_{10}$BrNO$_3$S: C, 34.30; H, 3.60; Br, 28.53; N, 5.00; S, 11.45%. Found: C, 34.47; H, 3.81; Br, 28.66; N, 4.99; S, 11.43%.

EXAMPLE 17

6$\beta$-Bromopenicillanic acid

A. Dicyclohexylammonium 6$\beta$-bromopenicillanate

To a solution of 6,6-dibromopenicillanic acid (10.8 g, 30 mmol) in dimethylsulphoxide (75 ml) was added sodium cyanoborohydride (2.1 g; 90% pure), and the mixture was stirred until a clear solution was obtained (about 30 minutes). After standing for 72 hours, the mixture was diluted with water (75 ml) to precipitate unreacted starting material as dimethylsulphoxide solvate (C$_8$H$_9$Br$_2$NO$_3$S, C$_2$H$_6$OS). The crystals were filtered off, washed with water and dried. The filtrate was extracted with methylene chloride (4×25 ml), and the combined extracts were washed with water (50 ml), dried (Na$_2$SO$_4$), and concentrated at reduced pressure to about half the volume. After addition of dicyclohexylamine (2.5 ml) and acetone (50 ml), the mixture was further concentrated to about 25 ml. Crystallization was induced by scratching, and, after standing for 1 hour at room temperature, the pure dicyclohexylammonium 6$\beta$-bromopenicillanate was filtered off, washed with acetone, and dried. The compound exhibited no well-defined melting point, after darkening at about 170° C., it decomposed at 280°–290° C.

B. 6$\beta$-Bromopenicillanic acid

A stirred suspension of dicyclohexylammonium 6$\beta$-bromopenicillanate in ethylacetate-water (1:1) (20 ml/g salt) was adjusted to pH 3 with 4N hydrochloric acid. Precipitated dicyclohexylammonium chloride was filtered off, and the organic layer was separated, washed twice with water, and dried. Addition of an equal volume of hexane followed by concentration of the solution at reduced pressure yielded pure, crystalline 6$\beta$-bromopenicillanic acid, identical with the compound described in Examples 12 and 16.

EXAMPLE 18

Sodium 6$\beta$-iodopenicillanate

A. 6,6-Diiodopenicillanic acid morpholine salt

To a stirred solution of 6-aminopenicillanic acid (110 g, ~0.5 mol) in a mixture of 5N sulphuric acid (400 ml) and methylene chloride (1.5 liter) were added dropwise and simultaneously at 0° C. 2.5M aqueous sodium nitrite (340 ml) and 0.5M methanolic iodine (1 liter). After the addition was finished, the cooling bath was removed, and stirring of the mixture was continued for 1 hour. The organic layer was separated, and the aqueous phase was extracted with methylene chloride (200 ml). The combined organic extracts were washed with 1M aqueous sodium thiosulphate (600 ml) and dried (Na$_2$SO$_4$). After addition of morpholine (32.6 ml, 0.375 mol), the resulting solution was concentrated at reduced pressure to about 200–250 ml to afford, after cooling, the title compound as colourless crystals which were collected, washed with acetone, and dried. Yield: 162.6 g; melting point: 152°–154° C. (decomposition).

Calculated for C$_{12}$H$_{18}$I$_2$N$_2$O$_4$S: C, 26.68; H, 3.36; I, 46.99; N, 5.19; S, 5.94%. Found: C, 27.01; H, 3.44; I, 46.70; N, 5.18; S, 5.64%.

B. Sodium 6$\beta$-iodopenicillanate

A stirred solution of 6,6-diiodopenicillanic acid morpholine salt (54 g, 0.1 mol) in methylene chloride (500 ml) was protected from light, and cetyl trimethylammonium boranate (36 g, 0.12 mol) was added. After stirring for 15 minutes at room temperature, the mixture was evaporated in vacuo. The residue was triturated with acetone (250 ml), insoluble salt was removed by filtration and the filtrate evaporated to dryness. The residual oil was dissolved in ethyl acetate (200 ml), water (200 ml) was added, and the pH in the aqueous phase was adjusted to 7 by addition of 2N sodium hydroxide with stirring. The aqueous layer was separated, the organic phase washed with water (50 ml), and the pH of the combined aqueous phases was adjusted to 3 with dilute hydrochloric acid under a layer of ether (200 ml). The organic phase was separated, the aqueous phase was re-extracted with ether, and the combined ethereal extracts were dried and concentrated at reduced pressure to about 80–100 ml. The concentrate contained a mixture of 6$\beta$- and 6$\alpha$-iodopenicillanic acids as well as minor amounts of penicillanic acid (approximate ratio 50:40:10) which were separated by dry column chromatography using a similar procedure as described in Example 1. The pure 6$\beta$-iodo acid thus obtained gave, after salt formation with 0.5M aqueous sodium bicarbonate and removal of water by azeotropic distillation with n-butanol, crystalline sodium 6$\beta$-iodopenicillanate; $[\alpha]_D^{20}$ +274° (c=0.5, 1M phosphate buffer pH 7).

Calculated for C$_8$H$_9$INNaO$_3$SI: C, 27.52; H, 2.60; I, 36.35; N, 4.01; S, 9.18%. Found: C, 27.31; H, 2.64; I, 36.12; ;1 N, 3.92; S, 9.34%.

EXAMPLE 19

6$\beta$-Iodopenicillanic acid

A. 6,6-Diiodopenicillanic acid dimethylsulphoxide solvate

To a cooled solution of 6,6-diiodopenicillanic acid morpholine salt (10.8 g, 20 mmol) in dimethylsulphoxide (20 ml) was added 1N hydrochloric acid (20 ml), and crystallization was induced by scratching. After further addition of water (20 ml), the crystals were filtered off, washed with water, and dried to give an almost quantitative yield of the title compound which showed an ill-defined melting point with slow decomposition above 120°–125° C.

Calculated for C$_8$H$_9$I$_2$NO$_3$S, C$_2$H$_6$OS: C, 22.61; H, 2.85; I, 47.78; N, 2.64; S, 12.07%. Found: C, 22.96; H, 2.81; I, 47.64; N, 2.74; S, 12.14%.

B. Dicyclohexylammonium 6$\beta$-iodopenicillanate

To a solution of 6,6-diiodopenicillanic acid dimethylsulphoxide solvate (5.31 g, 10 mmol) in dimethylsulphoxide (25 ml) was added sodium cyanoborohydride (0.7 g; 90% pure), and the mixture was stirred until a clear solution was obtained (about 30 minutes). After standing for 40 hours at room temperature, water (50 ml) was added, and the mixture was cooled to 5° C. to precipitate unreacted starting material which was collected, washed with water, and dried. The filtrate was extracted with methylene chloride (3×25 ml), and the combined extracts were washed with water (2×10 ml), dried (Na$_2$SO$_4$), and carefully evaporated in vacuo. The residual oil was dissolved in acetone (25 ml), an equivalent amount of dicyclohexylamine was added, and crystallization was induced by scratching. After standing for 1 hour, the pure dicyclohexylammonium 6β-iodopenicillanate was filtered off, washed with acetone, and dried. The compound showed no well-defined melting point, after darkening at about 150° C., it decomposed slowly above this temperature.

C. 6β-Iodopenicillanic acid

By substituting dicyclohexylammonium 6β-iodopenicillanate for the corresponding 6β-bromopenicillanate in the procedure of Example 17 B, 6β-iodopenicillanic acid was obtained as colourless crystals. Recrystallization from ether-diiospropyl ether afforded the analytical sample, $[\alpha]_D^{20} + 278°$ (c=0.5, CHCl$_3$).

Calculated for C$_8$H$_{10}$INO$_3$S: C, 29.37; H, 3.08; I, 38.79; N, 4.28; S, 9.80%. Found: C, 29.46; H, 3.13; I, 38.96; N, 4.27; S, 9.81%.

EXAMPLE 20

Pivaloyloxymethyl 6β-bromopenicillanate

A. Pivaloyloxymethyl 6,6-dibromopenicillanate

To a solution of potassium 6,6-dibromopenicillanate (5.96 g, 15 mmol) in dimethylformamide (30 ml) was added chloromethyl pivalate (2.22 ml, 15 mmol), and the mixture was stirred for 16 hours at room temperature. After dilution with ethyl acetate (120 ml), the mixture was washed with water (4×30 ml), dried, decolourized by stirring with charcoal (0.5 g; 1 hour), and evaporated to dryness to give the desired compound as a yellow oil which crystallized from ether-hexane; melting point: 101°–102° C.

B. Pivaloyloxymethyl 6β-bromopenicillanate

To a solution of pivaloyloxymethyl 6,6-dibromopenicillanate (5.68 g, 12 mmol) in dimethylsulphoxide (25 ml) was added sodium cyanoborohydride (0.84 g; 90% pure), and the mixture was stirred for 24 hours at room temperature in a dark room. After addition of water (75 ml), the mixture was extracted with ether (3×25 ml), and the combined ethereal extracts were washed with water (3×10 ml), dried, and concentrated at reduced pressure to about 20 ml. The concentrate was subjected to column chromatography on silica gel similar to the procedure described in Example 9C. Hereby, the 6β-bromo compound was separated from unreacted starting material. Fractions containing the more polar 6β-bromo ester were combined and evaporated in vacuo. The residual oil was crystallized from ether-diisopropyl ether to give pivaloyloxymethyl 6β-bromopenicillanate, melting point: 66°–68° C., identical with the compound described in Example 9C.

EXAMPLE 21

6β-Bromopenicillanic acid pivampicillin salt

To a stirred solution of pivampicillin hydrochloride (2.50 g, 5 mmol) in water (100 ml) was added dropwise 0.1M aqueous potassium 6β-bromopenicillanate (50 ml). The colourless precipitate thus obtained was filtered off, washed with water (3×10 ml), and dried in vacuo to give the pure title compound as colourless crystals which began to decompose at 120°–130° C. without melting.

The IR-spectrum (KBr) showed bands at 3030, 2970, 2935, 2870, 1790, 1770, 1680, 1600, and 627 cm$^{-1}$.

The NMR-spectrum (CDCl$_3$) showed signals at δ=1.20 (s, 9H; C(CH$_3$)$_3$), 1.36 (s, 3H; CH$_3$-2), 1.44 (s, 3H; CH$_3$-2), 1.52 (s, 3H; CH$_3$-2), 1.54 (s, 3H; CH$_3$-2), 4.26 (s, 1H; CH-3), 4.40 (s, 1H; CH-3), 5.11 (s, 1H; CHCO), 5.23, 5.36, 5.43, and ~5.76 (4 doublets, J=3.8–4.2 Hz, 4H; CH-5 and CH-6), 5.79 (ABq, J=5.5 Hz, 2H; OCH$_2$O), 7.40 (s, 5H; arom. CH), and 7.82 (d, J=8.2 Hz, 1H; CONH) ppm. Tetramethylsilane was used as internal reference.

EXAMPLE 22

6β-Iodopenicillanic acid bacampicillin salt

A solution of potassium 6β-iodopenicillanate (0.73 g, 2 mmol) in water (20 ml) was added dropwise to a stirred solution of bacampicillin hydrochloride (1.0 g, 2 mmol) in water (40 ml). The resulting crystalline precipitate was filtered off, washed with water, and dried to afford the pure title compound which decomposed at 110°–120° C. without melting.

The IR-spectrum (KBr) showed bands at 3030, 2980, 2870, 1780, 1765, 1695, 1625, and 618 cm$^{-1}$.

The NMR-spectrum (CDCl$_3$) showed signals at δ=1.31 (t, J=7 Hz, 3H; OCH$_2$CH$_3$), 1.38 (s, 3H; CH$_3$-2), 1.49 (s, 3H; CH$_3$-2), 1.54 (s, 3H; CH$_3$-2), 1.59 (s, 3H; CH$_3$-2), 4.25 (m, 4H; OCH$_2$CH$_3$ and CH-3), 4.99 (s, 1H; CHCO), 5.12 (bs, NH$_3^+$), 5.21, 5.45, 5.54, and 5.64 (4 doublets, J=3.8–4.2 Hz, 4H; CH-5 and CH-6), 6.76 (ABq, J=5.5 Hz, 1H; CHCH$_3$), 7.39 (s, 5H; arom. CH), and 7.72 (d, J=8.5 Hz, 1H; CONH) ppm. Tetramethylsilane was used as internal reference.

EXAMPLES 23–25

Further salts of 6β-halopenicillanic acids with inorganic bases

Treatment of an ethereal solution of the 6β-halopenicillanic acid with an equivalent amount of aqueous base followed by separation of the aqueous phase and freeze-drying afforded the salts listed in Table IV as colourless powders.

TABLE IV

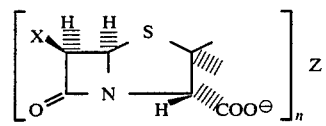

| Example | X | n | Z |
|---------|---|---|---|
| 23a | Cl | 1 | Na$^+$ |
| 23b | Cl | 2 | Ca$^{++}$ |
| 24a | Br | 1 | Li$^+$ |
| 24b | Br | 2 | Ca$^{++}$ |
| 25a | I | 1 | Li$^+$ |
| 25b | I | 2 | Ca$^{++}$ |

EXAMPLES 26–28

Further salts of 6β-halopenicillanic acids with organic bases

By treatment of a solution of the 6β-halopenicillanic acid in a suitable organic solvent, e.g. acetone, ethyl acetate or ether, with an equivalent amount of the organic base (preferably dissolved in the same solvent), the desired salt was obtained as a crystalline precipitate which was filtered off and dried in vacuo. The salts obtained by this method are listed in Table V below.

TABLE V

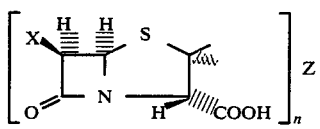

| Example | X | n | Z |
| --- | --- | --- | --- |
| 26a | Cl | 1 | dicyclohexylamine |
| 26b | Cl | 2 | N,N'—dibenzylethylenediamine |
| 27a | Br | 1 | morpholine |
| 27b | Br | 2 | N,N'—dibenzylethylenediamine |
| 27c | Br | 1 | N—ethylpiperidine |
| 27d | Br | 1 | procaine |
| 28a | I | 1 | dibenzylamine |
| 28b | I | 2 | N,N'—dibenzylethylenediamine |
| 28c | I | 1 | N—methylbenzylamine |
| 28d | I | 1 | procaine |

EXAMPLES 29–30

Salts of 6$\beta$-halopenicillanic acids with $\beta$-lactam antibiotics and pro-drugs thereof containing a basic group The salts listed in Table VI below were prepared by procedures similar to those described in the preceeding Examples 21–22 (A), 23–25 (B), or 26–28 (C).

TABLE VI

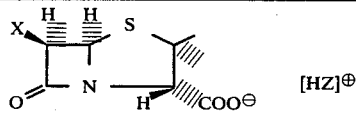

| Example | X | Z | Procedure | IR-data (cm$^{-1}$) |
| --- | --- | --- | --- | --- |
| 29a | Br | Bacampicillin | A | 3010, 2980, 2940, 1785, 1765, 1690, 1620, 628 |
| 29b | Br | Pivmecillinam | C | 2970, 2932, 2865, 1775, 1690, 1630, 1600, 625 |
| 29c | Br | Bacmecillinam | C | 2970, 2935, 2860, 1770, 1685, 1630, 1600, 628 |
| 29d | Br | Penethamate | C | 3455, 3020, 2940, 2860, 2660, 1800, 1780, 1745, 1675, 625 |
| 29e | Br | Ampicillin | B | |
| 29f | Br | Amoxycillin | B | |
| 30a | I | Pivampicillin | A | 3040, 2975, 2935, 2870, 1782, 1770, 1685, 1600, 618 |
| 30b | I | Pivmecillinam | C | 2970, 2935, 2865, 1780, 1770, 1685, 1630, 1600, 616 |
| 30c | I | Bacmecillinam | C | 2970, 2930, 2860, 1775, 1760, 1685, 1630, 1600, 616 |
| 30d | I | Penethamate | C | 3460, 3018, 2940, 2855, 2665, 1795, 1775, 1745, 1670, 615 |
| 30e | I | Ampicillin | B | |
| 30f | I | Amoxycillin | B | |

EXAMPLE 31

| Tablets | |
| --- | --- |
| Component | Per tablet |
| 6$\beta$-Iodopenicillanic acid sodium salt | 250 mg |
| Microcrystalline cellulose | 110 mg |
| Hydroxypropyl cellulose | 5 mg |
| Alginic acid | 10 mg |
| Talc | 23 mg |
| Magnesium stearate | 2 mg |
| | 400 mg |

The active component is blended with the microcrystalline cellulose, granulated with a 10% solution of hydroxypropyl cellulose in isopropanol, dried at 40° C., and screened through 1 mm sieves. Alginic acid, talc, and magnesium stearate are added, and the mixture is compressed into tablets each weighing 400 mg. The tablets are covered with a film-coating of hydroxypropyl methyl cellulose.

EXAMPLE 32

| Tablets | |
| --- | --- |
| Component | Per tablet |
| 6$\beta$-Bromopenicillanic acid sodium salt | 250 mg |
| Microcrystalline cellulose | 110 mg |
| Hydroxypropyl cellulose | 5 mg |
| Alginic acid | 10 mg |
| Talc | 23 mg |
| Magnesium stearate | 2 mg |
| | 400 mg |

By the same method as described in Example 31, the tablets containing 6$\beta$-bromopenicillanic acid sodium salt are obtained.

EXAMPLE 33

| Parenteral formulation | |
| --- | --- |
| Component | Per vial |
| 6$\beta$-Iodopenicillanic acid sodium salt | 125 mg |

The sterile crystalline component is filled into sterile vials which are aseptically sealed. For parenteral administration, 2 ml of sterile physiological saline is added to the content of the vial.

EXAMPLE 34

| Parenteral formulation | |
| --- | --- |
| Component | Per vial |
| 6$\beta$-Bromopenicillanic acid sodium salt | 125 mg |

The above formulation is obtained by the same method as described in Example 33.

EXAMPLE 35

| Capsules | |
| --- | --- |
| Component | Per capsule |
| 6$\beta$-Iodopenicillanic acid potassium salt | 125 mg |
| Hydroxypropyl cellulose | 3 mg |
| Talc | 6 mg |
| Magnesium stearate | 1 mg |
| | 135 mg |

The active ingredient is granulated with a solution of hydroxypropyl cellulose in isopropanol, dried at 40° C., and screened through 1 mm sieves. Talc and magnesium stearate are added, the components are well mixed to obtain a uniform blend, and 135 mg of the blend is filled in a No. 3 hard gelatine capsule.

EXAMPLE 36

| Capsules | |
| --- | --- |
| Component | Per capsule |
| 6$\beta$-Bromopenicillanic acid pivampi- | 250 mg |

-continued

| Capsules | |
|---|---|
| Component | Per capsule |
| cillin salt | |
| Hydroxypropyl cellulose | 5 mg |
| Talc | 23 mg |
| Magnesium stearate | 2 mg |
| | 280 mg |

The active compound is granulated with a solution of hydroxypropyl cellulose in isopropanol, dried at 40° C., and screened through 1 mm sieves. The diluents are added, and the mixture is carefully blended, 280 mg of the blend being filled in No. 2 gelatine capsules.

EXAMPLE 37

| Tablets | |
|---|---|
| Component | Per tablet |
| 6β-Iodopenicillanic acid sodium salt | 125 mg |
| Ampicillin | 250 mg |
| Corn starch | 75 mg |
| Hydroxypropyl cellulose | 10 mg |
| Alginic acid | 10 mg |
| Talc | 20 mg |
| Magnesium stearate | 5 mg |
| | 495 mg |

In the above composition, the active components are blended with corn starch, granulated with a 10% solution of hydroxypropyl cellulose in isopropanol, dried at 40° C., and screened through 1 mm screens. Alginic acid, talc, and magnesium stearate are added, and the mixture is compressed into tablets each weighing 495 mg. The tablets are covered with a film-coating of hydroxypropyl methyl cellulose.

EXAMPLE 38

| Tablets | |
|---|---|
| Component | Per tablet |
| 6β-Bromopenicillanic acid potassium salt | 125 mg |
| Ampicillin | 250 mg |
| Corn starch | 75 mg |
| Hydroxypropyl cellulose | 10 mg |
| Alginic acid | 10 mg |
| Talc | 20 mg |
| Magnesium stearate | 5 mg |
| | 495 mg |

By the same method as described in Example 37, the tablets containing 6β-bromopenicillanic acid potassium salt and ampicillin are obtained.

EXAMPLE 39

| Tablets | |
|---|---|
| Component | Per tablet |
| 6β-Iodopenicillanic acid potassium salt | 200 mg |
| Pivampicillin free base | 250 mg |
| Corn starch | 100 mg |
| Hydroxypropyl cellulose | 5 mg |
| Methyl cellulose | 5 mg |
| Alginic acid | 15 mg |
| Talc | 20 mg |
| Magnesium stearate | 5 mg |
| | 600 mg |

In the above composition, 6β-iodopenicillanic acid potassium salt and half the amount of corn starch are blended, granulated with a 10% solution of hydroxypropyl cellulose in isopropanol, dried at 40° C. and screened through 1 mm screens. The balance of corn starch is blended with pivampicillin, granulated with paste of methyl cellulose and water, dried at 50° C., and screened through 0.7 mm screens. The granulates are blended with alginic acid, talc, and magnesium stearate, and the mixture is compressed into tablets each weighing 600 mg. The tablets are covered with a film-coating of hydroxypropyl methyl cellulose.

EXAMPLE 40

| Tablets | |
|---|---|
| Component | Per tablet |
| 6β-Bromopenicillanic acid sodium salt | 150 mg |
| Pivampicillin free base | 250 mg |
| Corn starch | 100 mg |
| Hydroxypropyl cellulose | 5 mg |
| Methyl cellulose | 5 mg |
| Alginic acid | 15 mg |
| Talc | 20 mg |
| Magnesium stearate | 5 mg |
| | 550 mg |

The tablets containing 6β-bromopenicillanic acid sodium salt and pivampicillin free base are obtained by the same method as described in Example 39.

EXAMPLE 41

| Tablets | |
|---|---|
| Component | Per tablet |
| 6β-Iodopenicillanic acid sodium salt | 125 mg |
| Amoxycillin | 250 mg |
| Corn starch | 80 mg |
| Hydroxypropyl cellulose | 10 mg |
| Alginic acid | 10 mg |
| Talc | 20 mg |
| Magnesium stearate | 5 mg |
| | 500 mg |

The active ingredients are blended with the corn starch, granulated with a 10% solution of hydroxypropyl cellulose in isopropanol, dried at 40° C., and screened through 1 mm screens. After addition of alginic acid, talc, and magnesium stearate, the mixture is compressed into tablets each weighing 500 mg. The tablets are covered with a film-coating of hydroxypropyl methyl cellulose.

EXAMPLE 42

| Tablets | |
|---|---|
| Component | Per tablet |
| 6β-Bromopenicillanic acid potassium salt | 125 mg |
| Amoxycillin | 250 mg |
| Corn starch | 80 mg |
| Hydroxypropyl cellulose | 10 mg |
| Alginic acid | 10 mg |
| Talc | 20 mg |
| Magnesium stearate | 5 mg |
| | 500 mg |

By the same method as described in Example 41, the tablets containing 6β-bromopenicillanic acid potassium salt and amoxycillin are obtained.

EXAMPLE 43

| Tablets | |
|---|---|
| Component | Per tablet |
| 6β-Iodopenicillanic acid pivampicillin salt | 500 mg |
| Hydroxypropyl cellulose | 10 mg |
| Microcrystalline cellulose | 200 mg |
| Magnesium stearate | 10 mg |
| | 710 mg |

The active component is granulated with a 15% solution of hydroxypropyl cellulose and isopropanol, dried at 40° C., and screened through 1 mm sieves. Microcrystalline cellulose and magnesium stearate are added, and the mixture is compressed into tablets each weighing 710 mg.

EXAMPLE 44

| Tablets | |
|---|---|
| Component | Per tablet |
| 6β-Bromopenicillanic acid pivmecillinam salt | 350 mg |
| Hydroxypropyl cellulose | 10 mg |
| Microcrystalline cellulose | 130 mg |
| Magnesium stearate | 10 mg |
| | 500 mg |

The tablets containing the pivmecillinam salt of 6β-bromopenicillanic acid are obtained by the same method as described in Example 43.

EXAMPLE 45

| Tablets | |
|---|---|
| Component | Per tablet |
| 6β-Iodopenicillanic acid potassium salt | 125 mg |
| Cephalexin | 250 mg |
| Corn starch | 80 mg |
| Hydroxypropyl cellulose | 10 mg |
| Alginic acid | 10 mg |
| Talc | 20 mg |
| Magnesium stearate | 5 mg |
| | 500 mg |

The tablets containing 6β-iodopenicillanic acid potassium salt and Cephalexin are obtained by the same method as described in Example 41.

EXAMPLE 46

| Tablets | |
|---|---|
| Component | Per tablet |
| 6β-Bromopenicillanic acid sodium salt | 125 mg |
| Cefaclor | 250 mg |
| Corn starch | 80 mg |
| Hydroxypropyl cellulose | 10 mg |
| Alginic acid | 10 mg |
| Talc | 20 mg |
| Magnesium stearate | 5 mg |
| | 500 mg |

By the same method as described in Example 41, the tablets containing 6β-bromopenicillanic acid sodium salt and Cefaclor are obtained.

EXAMPLE 47

6β-Iodopenicillanic acid sodium salt/Pivmecillinam HCl

Two-layer tablets

| Granulate I | |
|---|---|
| Component | Per tablet |
| 6β-Iodopenicillanic acid sodium salt | 100 mg |
| Hydroxypropyl cellulose | 2 mg |
| Dicalcium phosphate dihydrate | 86 mg |
| Sodium starch glycolate | 10 mg |
| Magnesium stearate | 2 mg |

The 6β-iodopenicillanic acid sodium salt is granulated with a solution of hydroxypropyl cellulose in isopropanol, dried at 40° C., and screened through 0.75 mm screens. The granules are blended with dicalcium phosphate dihydrate, sodium starch glycolate and magnesium stearate.

| Granulate II | |
|---|---|
| Component | Per tablet |
| Pivmecillinam hydrochloride | 100 mg |
| Hydroxypropyl cellulose | 2 mg |
| Microcrystalline cellulose | 50 mg |
| Magnesium stearate | 1.5 mg |
| Talc | 3.5 mg |

Pivmecillinam hydrochloride is granulated with a solution of hydroxypropyl cellulose, dried at 40° C., and screened through 0.75 mm screens. The granules are blended with microcrystalline cellulose, magnesium stearate, and talc.

The granulates are compressed into two-layer tablets containing 200 mg of granulate I as the bottom layer and 157 mg of granulate II as the top layer.

The tablets are film-coated with hydroxypropylmethyl cellulose dissolved in ethanol-water (1:1).

EXAMPLE 48

6β-Bromopenicillanic acid sodium salt/Pivampicillin base

Two-layer tablets

| Granulate I | |
|---|---|
| Component | Per tablet |
| 6β-Bromopenicillanic acid sodium salt | 100 mg |
| Polyvinyl pyrrolidone | 5 mg |
| Dicalcium phosphate dihydrate | 85 mg |
| Sodium starch glycolate | 8 mg |
| Magnesium stearate | 2 mg |

The 6β-bromopenicillanic acid sodium salt is granulated with a solution of polyvinyl pyrrolidone in isopropanol, dried at 40° C., screened through 0.75 mm screens, and blended with dicalcium phosphate dihydrate, starch, and magnesium stearate.

| Granulate II | |
|---|---|
| Component | Per tablet |
| Pivampicillin base | 125 mg |
| Starch | 30 mg |
| Hydroxypropyl cellulose | 3.5 mg |
| Magnesium stearate | 1.5 mg |

The pivampicillin base and 10 mg of the starch are blended and granulated with a solution of hydroxypropyl cellulose in de-ionized water, dried at 50° C., and screened through 0.75 mm screens. The granules are blended with the rest of the starch and magnesium stearate.

The granulates are compressed into tablets containing 200 mg of granulate I as the bottom layer and 160 mg of granulate II as the top layer. The tablets are film-coated with hydroxypropylmethyl cellulose dissolved in de-ionized water-ethanol (1:1).

EXAMPLE 49

6$\beta$-Bromopenicillanic acid sodium salt/Amoxycillin Two-layer tablets

| Granulate I | |
|---|---|
| Component | Per tablet |
| 6$\beta$-Bromopenicillanic acid sodium salt | 100 mg |
| Polyvinyl pyrrolidone | 7 mg |
| Lactose | 50 mg |
| Silicium dioxide | 1.5 mg |
| Magnesium stearate | 1.5 mg |

The 6$\beta$-bromopenicillanic acid sodium salt is granulated with a solution of polyvinyl pyrrolidone in isopropanol, dried at 40° C., and screened through 0.75 mm screens. The granules are blended with lactose, silicium dioxide and magnesium stearate.

| Granulate II | |
|---|---|
| Component | Per tablet |
| Amoxycillin | 200 mg |
| Starch | 30 mg |
| Polyvinyl pyrrolidone | 6 mg |
| Silicium dioxide | 2 mg |
| Magnesium stearate | 2 mg |

Amoxycillin is blended with starch, granulated with a solution of polyvinyl pyrrolidone in de-ionized water, dried at 50° C., and screened through 0.75 mm screens. The granules are blended with silicium dioxide and magnesium.

The granulates are compressed into tablets containing 240 mg of granulate II as the bottom layer and 160 mg of granulate I as the top layer.

EXAMPLE 50

6$\beta$-Iodopenicillanic acid sodium salt/Pivmecillinam HCl/Pivampicillin
Three-layer tablets

| Granulate I | |
|---|---|
| Component | Per tablet |
| 6$\beta$-Iodopenicillanic acid sodium salt | 100 mg |
| Hydroxypropyl cellulose | 2 mg |
| Microcrystalline cellulose | 50 mg |
| Sodium starch glycolate | 6 mg |
| Magnesium stearate | 2 mg |

6$\beta$-Iodopenicillanic acid sodium salt is granulated with a solution of hydroxypropyl cellulose in isopropanol, dried at 40° C., and screened through 0.75 mm screens, whereafter microcrystalline cellulose, sodium starch glycolate, and magnesium stearate are added.

| Granulate II | |
|---|---|
| Component | Per tablet |
| Pivmecillinam hydrochloride | 100 mg |
| Hydroxypropyl cellulose | 2 mg |
| Microcrystalline cellulose | 50 mg |
| Magnesium stearate | 1.5 mg |

Pivmecillinam hydrochloride is granulated with a solution of hydroxypropyl cellulose in isopropanol, dried at 40° C., and screened through 0.75 mm screens. The granules are blended with microcrystalline cellulose and magnesium stearate.

| Granulate III | |
|---|---|
| Component | Per tablet |
| Pivampicillin base | 125 mg |
| Starch | 24 mg |
| Hydroxypropyl cellulose | 3.5 mg |
| Sodium starch glycolate | 7 mg |
| Magnesium stearate | 1.5 mg |

The pivampicillin base and 10 mg starch are blended and granulated with a solution of hydroxypropyl cellulose dissolved in de-ionized water, the granulated mass being dried at 50° C., and screened through 0.75 mm screens. Thereafter sodium starch glycolate, the rest of the starch, and magnesium stearate are added.

The granulates are compressed into tablets containing 160 mg of granulate I as the bottom layer, 153.5 mg of granulate II as the intermediate layer, and 161 mg of granulate III as the top layer. The tablets are covered with a film-coating of hydroxypropylmethyl cellulose dissolved in de-ionized water-ethanol (1:1).

What we claim is:
1. Substantially pure dicyclohexylammonium 6$\beta$-bromopenicillanate.

* * * * *